United States Patent [19]

Umeda et al.

[11] Patent Number: 5,362,892

[45] Date of Patent: Nov. 8, 1994

[54] PHOSPHOLIPID COMPOSITION, FAT AND OIL COMPOSITION CONTAINING THE SAME AND PROCESS FOR PRODUCING PHOSPHATIDIC ACIDS

[75] Inventors: Tomoshige Umeda; Hideki Yokomichi; Hideki Mori; Takuji Yasukawa; Yoshihisa Katsuragi; Yuki Mitsui; Yasuhiro Miura, all of Ibaraki, Japan

[73] Assignee: Kao Corporation, Tokyo, Japan

[21] Appl. No.: 196,992

[22] Filed: Jan. 26, 1994

Related U.S. Application Data

[63] Continuation of Ser. No. 822,983, Jan. 21, 1992, abandoned.

[30] Foreign Application Priority Data

Jan. 18, 1991 [JP] Japan .................................. 3-004412
Feb. 14, 1991 [JP] Japan .................................. 3-020707
Feb. 22, 1991 [JP] Japan .................................. 3-028418

[51] Int. Cl.$^5$ .............................................. C09F 9/02
[52] U.S. Cl. .......................................... 554/82; 554/80; 554/83
[58] Field of Search .............................. 554/80, 82, 83

[56] References Cited

U.S. PATENT DOCUMENTS 4,479,977 10/1984 Dashiell et al. .................... 426/609

FOREIGN PATENT DOCUMENTS 0049914 4/1982 European Pat. Off. .
0259495 3/1988 European Pat. Off. .
0287281 10/1988 European Pat. Off. .
0329327 8/1989 European Pat. Off. .
0372327 6/1990 European Pat. Off. .
0378893 7/1990 European Pat. Off. .
399544 11/1990 European Pat. Off. .
WO8904314 5/1989 WIPO .

OTHER PUBLICATIONS

DATABASE WPIL, Section Ch, Week 8714, Derwent Publishing Ltd., London, GB; Class D, AN 87-099010 & JP-A-62 048 390 (Nisshin Oil Mills KK) Mar. 3, 1987.

Primary Examiner—JoseACUie/ G. Dees
Assistant Examiner—Deborah D. Carr
Attorney, Agent, or Firm—Sughrue, Mion, Zinn, Macpeak & Seas

[57] ABSTRACT

A phospholipid composition which satisfies the following requirements (i) and (ii):

(i) a weight ratio of a nitrogen-containing phospholipid to the sum of a phospholipid, a glycolipid and a sterol derivative of less than 0.5; and (ii) a ratio of an area of a high-polar substance on a silica gel thin-layer chromatogram to the sum of areas of a phospholipid, a glycolipid and a sterol derivative on a silica gel thin-layer chromatogram of less than 500 area/$\mu$g. A fat and oil composition containing from 0.001 to 30% by weight of the phospholipid composition is also disclosed. The present invention enables the blending of phospholipids with a frying oil, which has been considered difficult since it causes heat coloration. Thus a fat and oil composition, which is excellent in mold-release characteristics during cooking, has a good smell during heating, suffers from no coloration of oil after heating and shows a good flavor, can be obtained. A process for producing phosphatidic acids and lysophosphatidic acids is further disclosed.

18 Claims, No Drawings

PHOSPHOLIPID COMPOSITION, FAT AND OIL COMPOSITION CONTAINING THE SAME AND PROCESS FOR PRODUCING PHOSPHATIDIC ACIDS

This is a continuation of application Ser. No. 07/822,983 filed Jan. 21, 1992, now abandoned.

FIELD OF THE INVENTION

This invention relates to a phospholipid composition and a fat and oil composition containing the same. More particularly, it relates to an edible phospholipid composition which is excellent in preventing the adhesion of a material to a heating device during heating and shows a remarkably improved color even after heating. In particular, the phospholipid composition of the present invention is excellent in preventing the adhesion of a food material to a cooking device (for example, baking mold, baking plate) during heating and in suppressing sputtering during a cooking process, has a good flavor and does not suffer from any browning or coloration of phospholipids due to heating or generation of any offensive smell caused by the thermal decomposition or denaturation of phospholipids.

This invention also relates to a process for producing phosphatidic acids (hereinafter sometimes referred to simply as PAs) and/or lysophosphatidic acids (hereinafter sometimes referred to simply as L-PAs) of a high purity.

BACKGROUND OF THE INVENTION

Phospholipids, which are basic substances constituting biomembranes, belong to lipids controlling the fundamental living activities, for example, protection of cell tissues, mediation of information, adjustment of material transfer.

In recent years, it has attracted scientific and industrial attraction that various functional substances can be encapsulated in vesicles (or liposomes) consisting of phospholipids capable of forming bilayer membranes. In the field of pharmaceutical science and medicine, for example, it is expected that this phenomenon is applicable to a drug delivery system (DDS).

The present inventors have tried to apply such high-functional lipids to the food industry and they previously succeeded in the development of a cooking oil suffering from no sputtering and having good mold release characteristics as disclosed in JP-A-1-27431 (the term "JP-A" as used herein means an "unexamined published Japanese patent application").

Examples of the industrial application of PA include, furthermore, improvement of dough properties in a baking process as disclosed in JP-A-58-51853, production of an emulsifier comprising PA and a zein complex as disclosed in JP-A-62-204838, application to drugs as disclosed in JP-A-54-105222, JP-A-55-11582, JP-A-56-127308 and JP-A-60-255728, application to cosmetics as disclosed in JP-A-59-27809 and application to chemical products as disclosed in JP-A-53-108503 and JP-A-60-243171. Namely, attempts have been made to use PA in various industrial fields.

A known method for producing PA comprises treating lecithin with ground oilseeds or an oilseed extract. However, the product thus obtained is contaminated with impurities and thus should be purified. Phospholipids including PA and L-PA are commonly purified by column chromatography. In the purification by silicic acid column chromatography, in particular, each component can be eluted and fractionated by varying the polarity of the development solvent. A chloroform/methanol mixture is used as a development solvent for purifying PA and L-PA and these products are separated from each other by changing the polarity of the solvent by varying the mixing ratio. However, there arises a problem of the contamination with impurities and thus the product should be passed through the column several times in order to obtain a specimen of a high purity, which causes some disadvantages including an increase in the amount of the solvent to be used and a decrease in the yield. It is also proposed to separate PA and L-PA by thin layer chromatography and detecting each product with a non-decomposition reagent, followed by scratching and extracting the portion containing PA or L-PA from the plate. However, this method is seemingly ineffective from an industrial viewpoint, since the yield thus achieved is limited.

On the other hand, there has been known that lecithin is specifically effective, compared with a number of other surfactants, in improving the mold-release characteristics of food materials which are liable to undergo heat adhesion (for example, sponge cake dough, egg roll).

Typical examples of commonly employed lecithin, which comprises a phospholipid mixture comprising nitrogen-containing phospholipids (for example, phosphatidylcholine, phosphatidylethanolamine) as the main components, are obtained by extracting or purifying soybean, yolk or the like.

These natural lecithins such as soybean lecithin and yolk lecithin are unstable and undergo browning when heated to 150° C. or above, even in a fat-protected state, thus turning into a dark brown.

The present inventors found out that a fat and oil composition containing 0.1 % by weight or more of phospholipids, from which the nitrogen-containing phospholipids causing the heat coloration had been removed by, for example, an enzymatic treatment, would never undergo heat coloration when used in frizzling foods and have already applied the same for a patent (JP-A-2-27943).

However, a fat and oil composition containing from 0.01 to 30 % by weight of such phospholipids free from any nitrogen-containing phospholipids still suffers from disadvantages that the oil per se is seriously colored when used at a higher temperature for a long period of time (for example, in frying).

SUMMARY OF THE INVENTION

The present inventors have conducted extensive studies in order to solve the above problems. As a result, they have found that there are some substances causing heat coloration other than the nitrogen-containing phospholipids. As the results of detailed examinations on the coloring substances other than the nitrogen-containing phospholipids, it has been found out that high-polar substances remaining around the original point in normal phase thin-layer chromatography (hereinafter sometimes referred to as TLC) would cause the heat coloration of the oil per se.

Based on the above finding, a phospholipid composition, from which high-polar substances and nitrogen-containing phospholipids have been removed, is prepared by subjecting a starting material, which is a natural lecithin, preferably a lecithin treated with an enzyme (for example, phospholipase D, phospholipase A2) or fractionated so as to lower the contents of phosphatidylcholine (PC) and phosphatidylethanolamine (PE) and to elevate the contents of a phosphatidic acid (PA), a lysophosphatidic acid (L-PA) and a phosphatidylinositol (PI) to a definite level or above, to, for example, a column treatment. Then the present inventors have found that the fat and oil composition containing the phospholipid composition free from any high-polar substances or nitrogen-containing phospholipids would never undergo coloration of the oil per se, even when used as a frying oil at a high temperature, thus completing the present invention.

Accordingly, the present invention provides a phospholipid composition which satisfies the following requirements (i) and (ii):

(i) a weight ratio of a nitrogen-containing phospholipid to the sum of a phospholipid, a glycolipid and a sterol derivative of less than 0.5; and (ii) a ratio of an area of a high-polar substance in a silica gel thin-layer chromatogram to the sum of areas of a phospholipid, a glycolipid and a sterol derivative in a silica gel thin-layer chromatogram of less than 500 area/$\mu$g.

The present invention further provides a fat and oil composition containing from 0.001 to 30% by weight of the phospholipid composition as well as a fat and oil composition containing from 0.001 to 30% by weight of the phospholipid composition and from 5 to 99% by weight of a diglyceride component.

The present invention furthermore provides a process for producing phosphatidic acids and/or lysophosphatidic acids which comprises purifying a phospholipid mixture containing a phosphatidic acid and/or a lysophosphatidic acid in a purification step comprising a step (a) and then washing a polyvalent metal salt of the phosphatidic acid and/or the lysophosphatidic acid obtained in the step (a) with an aqueous water-soluble solvent under an acidic condition, wherein the step (a) comprises:

dispersing or dissolving the phospholipid mixture containing the phosphatidic acid and/or the lysophosphatidic acid in water or a nonpolar solvent and then reacting the phosphatidic acid and/or the lysophosphatidic acid with an aqueous solution of a polyvalent metal salt in the presence of a polar solvent under an alkaline condition to thereby give the polyvalent metal salt of the phosphatidic acid and/or the lysophosphatidic acid.

The present invention still furthermore provides a process for producing phosphatidic acids and/or lysophosphatidic acids which comprises purifying a phospholipid mixture containing a phosphatidic acid and/or a lysophosphatidic acid in a purification step comprising the step (a) and a step (b) and then washing a polyvalent metal salt of the phosphatidic acid and/or the lysophosphatidic acid obtained in the step (b) with an aqueous water-soluble solvent under an acidic condition, wherein the step (b) comprises:

adding a substance capable of precipitating a polyvalent metal salt of a phosphatidic acid and/or a lysophosphatidic acid into the polyvalent metal salt of the phosphatidic acid and/or the lysophosphatidic acid obtained in the step (a) in the presence of a nonpolar solvent to precipitate the polyvalent metal salt of the phosphatidic acid and/or the lysophosphatidic acid and then separating the polyvalent metal salt of the phosphatidic acid and/or the lysophosphatidic acid.

The expression "phosphatidic acids and lysophosphatidic acids" as used herein means a metal salt of a phosphatidic acid and a lysophosphatidic acid and a free phosphatidic acid and lysophosphatidic acid which do not contain metal atom(s).

DETAILED DESCRIPTION OF THE INVENTION

The term "high-polar substance" as used herein means those located around the original point (i.e., Rf value of from 0 to 0.1) in a silica gel thin layer chromatogram when a phospholipid is developed in silica gel thin-layer chromatography with chloroform-/acetone/methanol/acetic acid/water (10:4:2:2:1). Details of technique, procedures and the like for thin-layer chromatography which may be used in the present invention is disclosed, for example, in "Shishitsu Bunseki-Ho Nyumon (Course of Method for LipidAnalysis)", Seibutsu Kagaku Jikken-Ho (Method for Biochemical Experiment), volume 9, published by Gakkai Shuppan Center (1985). These high-polar substances involve various substances such as those having primary amine groups such as amino acids, those formed through the decomposition of polar moieties of phospholipids, as disclosed, for example, in Tomioka and Kaneda, Kagaku to Seibutsu (Chemical and Organism), 14, 509 (1976) and it is highly difficult to determine each of these substances. The content of the high-polar substances may be conveniently determined by thin layer chromatography. Namely, a silica gel plate developed in the above-mentioned manner is allowed to undergo color-development with the use of sulfuric acid and the area of spots on the thin-layer chromatogram thus developed is measured with a TLC scanner. The high-polar substance content is expressed by the value of the area thus measured in the unit of area/$\mu$g.

The term "phospholipid" as used herein involves a nitrogen-containing phospholipid and a phospholipid which does not contain any nitrogen atoms.

The term "phospholipid which does not contain any nitrogen atoms" as used herein means that containing a base which does not contain nitrogen atom and involves a phosphatidic acid (PA), a lysophosphatidic acid (L-PA), a phosphatidylinositol (PI) and a phosphatidylglycerol (PG).

The term "nitrogen-containing phospholipid" as used herein involves nitrogen-containing glycerophospholipids such as a phosphatidylcholine (PC), a phosphatidylethanolamine (PE) and a phosphatidylserine (PS) as well as a sphingophospholipids such as a sphingomyelin (SM).

The term glycolipid is used herein to mean a complex comprising sphingosines or similar amines, fatty acids and sugars (including amino sugars) and it can be classified roughly into (1) cerebrosides (galactolipids) (e.g., phrenosines), (2) sulfolipids (e.g., cerebron sulfuric acid) and (3) mucolipids (e.g., gangliosides and hematosides).

Further, the term "sterol derivative" involves a sitosterol, a stigmasterol and a cholesterol.

In the present invention, the phospholipids, glycolipids and sterol derivatives are separated from each other by chromatography and then determined.

It is required that the weight ratio of the content of nitrogen-containing phospholipids of the phospholipid composition of the present invention to the total amount of phospholipids and glycolipids and sterol derivatives, if contained, in the phospholipid composition is less than 0.5, preferably less than 0.05, and more preferably less than 0.01. It is further required that the content of the high-polar substances is less than 500 area/$\mu$g, preferably less than 200 area/$\mu$g, in the area value as specified above based on the total area value of the phospholipids, glycolipids and sterol derivatives. A content of the nitrogen-containing phospholipids or the high-polar substances exceeding the level as specified above is undesirable from the viewpoints of, for example, odor and coloration.

A phospholipid composition having the specific composition of the present invention can be obtained by, for example, a method in which a natural lecithin is used as a starting material, nitrogen-containing phospholipids (e.g., phosphatidylcholine, phosphatidylethanolamine) contained therein are decomposed with an enzyme (i.e., the formation of phosphatidic acid or lysophosphatidic acid), and then, the resulting products are fractionated with the use of a silicic acid column or an ion exchange column, as disclosed in "Seibutsu Kagaku [I]", *Shin-Jikken Kagaku Koza* (New Course of Experimental Chemistry), vol. 20, edited by The Chemical Society of Japan, page 457 (1985).

One of the most convenient and effective methods therefor comprises selectively decomposing nitrogen-containing phospholipids (e.g., phosphatidylcholine, phosphatidylethanolamine) in soybean lecithin or yolk lecithin with the use of phospholipase D which is contained, for example, in cabbage leaves in a large amount, thus lowering the contents of these nitrogen-containing phospholipids and simultaneously elevating the contents of phosphatidic acid, lysophosphatidic acid and/or salts thereof (for example, sodium salt, calcium salt) and then removing high-polar substances from the resulting phospholipids, which is almost free from nitrogen-containing phospholipids, by using a silicic acid column, as disclosed in The Journal of Biological Chemistry, 239, (12), pages 4066–4072 (1964).

Further, a phospholipid composition of the present invention can more conveniently and efficiently be obtained by a process comprising purifying a phospholipid mixture containing a phosphatidic acid and/or a lysophosphatidic acid in a purification step comprising a step (a) and then washing a polyvalent meal salt of the phosphatidic acid and/or the lysophosphatidic acid obtained in the step (a) with an aqueous water-soluble solvent under an acidic condition, wherein the step (a) comprises:

dispersing or dissolving the phospholipid mixture containing the phosphatidic acid and/or the lysophosphatidic acid in water or a nonpolar solvent and then reacting the phosphatidic acid and/or the lysophosphatidic acid with an aqueous solution of a polyvalent metal salt in the presence of a polar solvent under an alkaline condition to thereby give the polyvalent metal salt of the phosphatidic acid and/or the lysophosphatidic acid.

In this process, the polyvalent metal salt of the phosphatidic acid and/or the lysophosphatidic acid obtained in the step (a) may further be subjected purification in a step (b), which comprises:

adding a substance capable of precipitating a polyvalent metal salt of a phosphatidic acid and/or a lysophosphatidic acid into the polyvalent metal salt of the phosphatidic acid and/or the lysophosphatidic acid obtained in the step (a) in the presence of a nonpolar solvent to precipitate the polyvalent metal salt of the phosphatidic acid and/or the lysophosphatidic acid, and then separating the polyvalent metal salt of the phosphatidic acid and/or the lysophosphatidic acid.

The phospholipid mixture containing PA or L-PA is available as a commercial product. Alternatively, it can be obtained by treating lecithin with ground oilseeds or an oilseed extract. The ground oilseeds may be obtained by grinding oilseeds, while the oilseed extract may be obtained by extracting the ground oilseeds and optionally followed by penetration purification by permeating through, for example, a membrane. These treatments may preferably be performed in the presence of an inert gas. Conventionally known treatment methods may be employed therefor.

In the step (a), the phospholipid mixture containing the phosphatidic acid and/or the lysophosphatidic acid is dispersed or dissolved in water or a nonpolar solvent. The nonpolar solvent to be used in the present invention include a liquid organic compound containing 5 to 16 carbon atoms and having a dielectric constant of 10 or below. Examples of the liquid organic compound having a dielectric constant of 10 or below include hydrocarbons such as n-hexane and benzene, halogenated (e.g., a chlorine atom) hydrocarbons such as chloroform and hydrocarbons substituted with an aromatic hydrocarbon (e.g., phenyl) and the like, each containing 5 to 16 carbon atoms. Among them, hydrocarbons having 5 to 16 carbon atoms are preferred and n-hexane is particularly preferred in view of safety.

The dielectric constant as used herein is determined in accordance with the description on the dielectric constants of liquid organic compounds and liquids in *Kagaku Binran Kiso-Hen, Kaitei 2-Hah* (Chemical Handbook Basic Volume, the second revised edition), edited by Chemical Society of Japan (pages 1166–1168 and 1582–1583) (1975).

Subsequently, a mixture of an aqueous solution of a polyvalent metal salt and a polar solvent is added to the dispersion or solution of the phospholipid mixture in an amount of 0.1 time by volume or more, preferably 0.4 to 0.8 times by volume, based on the water or the nonpolar solvent. The volume ratio of the aqueous solution of the polyvalent metal salt to the polar solvent in this mixture may preferably be 0.1 or above, more preferably be from 0.5 to 2.0. The polar solvent to be used in this step includes a liquid organic compound containing 1 to 10 carbon atoms and having a dielectric constant exceeding 10. Examples of the liquid organic compound having a dielectric constant exceeding 10 include monohydric alcohols (e.g., methanol, ethanol), ketones (e.g., acetone) and polyhydric alcohols (e.g., ethylene glycol, glycerine) each containing 1 to 10 carbon atoms. In view of safety, it is particularly preferable to use ethanol therefor. Examples of the polyvalent metal salt to be contained in the aqueous solution of the polyvalent metal salt include chlorides, sulfates, carbonates and phosphates of elements of the group IIA (for example, Mg, Ca, Sr, Ba) and those of the group IIIB (for example, Al). Among these polyvalent metal salts, chlorides are preferable and Ca salts are more preferable. In particular, calcium chloride is suitable therefor. The concentration of the polyvalent metal salt aqueous solution may be 1 time by mol or above, preferably 1 to 7 times by mol, based on the mole number of the phospholipid mixture.

The resulting mixture is stirred under an alkaline condition at a pH value of 7.0 or above, preferably pH value of 10 to 12, at a temperature of 0° to 80° C., preferably a temperature of 0° to 40° C., for 0.5 hours or longer.

Thus a mixture containing the polyvalent metal salt of PA and/or L-PA is obtained.

In the purification step of the present invention, the polyvalent metal salt of PA and/or L-PA formed in the step (a) may further be subjected to the step (b) to selectively precipitate the polyvalent metal salt of PA and/or L-PA.

In the case where the mixture containing the polyvalent metal salt of PA and/or L-PA obtained in the step (a) is in the form of a solution of a nonpolar solvent, the nonpolar solvent phase containing the polyvalent metal salt of PA and/or L-PA is separated from the mixture by a known procedure such as allowing to stand or centrifugation and the resulting nonpolar solvent phase is then subjected to the step (b). In the case where the mixture obtained in the step (a) is in the form of an aqueous dispersion, the mixture is preliminary dehydrated, desolvated and dissolved in a nonpolar solvent to give a nonpolar solvent solution of the polyvalent metal salt of PA and/or L-PA and then the resulting nonpolar solution is subjected to the step (b). Examples of the nonpolar solvent to be used in this step include those employed in the step (a).

Next, a substance capable of precipitating polyvalent metal salt of PA and/or L-PA is added to the nonpolar solvent solution of the polyvalent metal salt of PA and/or L-PA in an amount of 0.1 time by volume or above, preferably from 0.1 to 2.0 times by volume, based on the nonpolar solvent solution to selectively precipitate the polyvalent metal salt of PA and/or L-PA. In this step, it is preferred that the nonpolar solvent containing the polyvalent metal salt of PA and/or L-PA is aged for 0.5 hours or longer under stirring. The polyvalent metal salt of PA and/or L-PA thus precipitated may be separated from the supernatant by known methods. When the amount of the added substance is less than 0.1 time by volume, the polyvalent metal salt of PA and/or L-PA are not precipitated. When the amount thereof exceeds 2.0 times by volume, on the other hand, impurities dissolved in the nonpolar solvent is extracted by the polar solvent, which lowers the purity of the obtained polyvalent metal salt of PA and/or L-PA.

As the substance capable of selectively precipitating a polyvalent metal salt of PA and/or L-PA, a lipid and a polar solvent containing 1 to 10 carbon atoms and having a polar group may be used. Examples of the lipids include monoglycerides, diglycerides, triglycerides and mixtures thereof. For instance, monoglycerides, diglycerides and triglycerides having saturated fatty acid residues or unsaturated fatty acid residues containing 8 to 24 carbon atoms may be used therefor. Among them, those having a slipping point, as defined in *Kijun Yushi Bunseki Siken Ho* (Standard Methods for the Analysis of Oils, Fats and Derivatives), Item 2.3.4.2-90, published by The Japan Oil Chemists' Society (1991), of less than 20° C. are preferably used, and, in view of safety, edible fats and oils, in particular, edible oils are more preferably used. Specific examples thereof include vegetable oils such as soybean oil, rapeseed oil, sunflower oil, corn oil, rice bran oil and cottonseed oil; and animal oils such as fish oil. As the polar solvent containing 1 to 10 carbon atoms and having a polar group, liquid organic compounds having a dielectric constant exceeding 10 may be used. The liquid organic compounds having a dielectric constant exceeding 10 include monohydric alcohols, ketones, polyhydric alcohols and a mixture thereof. Examples of the monohydric alcohols include methanol, ethanol and isopropanol. Examples of the ketones include acetone and methyl ethyl ketone. Examples of the polyhydric alcohols include ethylene glycol and glycerol. Among them, a monohydric alcohol is particularly preferred.

In order to elevate the purity of the polyvalent metal salt of PA or L-PA, it is preferable to repeat the step (b) twice or more. Namely, the obtained precipitate is further purified by dissolving again in a nonpolar solvent such as n-hexane and adding a substance capable of selectively precipitating the polyvalent metal salts of PA and/or L-PA, followed by separating the precipitated polyvalent metal salt of PA and/or L-PA.

After the completion of the purification, the precipitate is washed with an aqueous water-soluble solvent under an acidic condition. This washing may preferably be performed at a pH value of 0.5 to 5 at a temperature of 0° to 40° C. with the use of 5 times by weight or more, based on the solid matters, of the aqueous water-soluble solvent. Among the liquid organic compound containing 1 to 10 carbon atoms, which are exemplified above as the polar solvent, those having a dielectric constant exceeding 20 may be used as the water-soluble solvent to be used in this step. The liquid organic compounds having a dielectric constant exceeding 20 include monohydric alcohols, ketones, polyhydric alcohols and mixtures thereof. Examples of the monohydric alcohols include methanol, ethanol and isopropanol. Examples of the ketones include acetone and methyl ethyl ketone. Examples of the polyhydric alcohols include ethylene glycol and glycerol. Ethanol is preferably selected therefor. The ratio of water to the water-soluble solvent in the aqueous water-soluble solvent may preferably range from 5 to 80% by weight.

The polyvalent metal salt of PA and/or L-PA thus obtained may be formulated into various salt compounds such as sodium salts by a known salt-exchange procedure. Alternately, they may be desalted by a known method to thereby give free PA and/or L-PA which do not contain metal atoms.

The fat and oil composition of the present invention contains from 0.001 to 30% by weight of the phospholipid composition of the present invention. When the content of the phospholipid composition is less than 0.001% by weight, the effects of the present invention cannot be achieved in a fat and oil composition. On the other hand, a content of the phospholipid composition exceeding 30% by weight might cause some troubles in handling the fat and oil composition, for example, an increase in viscosity.

It is reasonable to regard the content of acetone-insoluble matters as the content of the phospholipids content in the fat and oil composition of the present invention because the content of acetone-insoluble matters is conventionally regarded as the total phospholipids content and this accords with the definition of the lecithin content specified in Shokuhin Tenkabutsu Koteisyo (Food Additives Official Book).

As the fat to be used in the fat and oil composition of the present invention, one or more materials may be selected from among, for example, vegetable oils such as soybean oil, rapeseed oil, palm oil, corn oil, cotton seed oil, coconut oil, palm kernel oil, rice bran oil, sesame oil, safflower oil, high-oleic safflower oil, sunflower oil and high-oleic sunflower oil; animal fats such as beef tallow, lard, fish oil, whale oil and milk fat; and those obtained by fractionating, hydrogenating or ester-exchanging these fats or oils.

It is preferable that the fat and oil composition of the present invention further contains from 5 to 99% by weight of a diglyceride component. As the diglyceride component to be used in the present invention, a composition which satisfies the followings requirements is preferred:

(1) a weight ratio of diglycerides to monoglycerides ranges from 5:1 to 990:1;

(2) diglycerides are contained so as to give a content, based on the total of the fats or oil composition, of from 5 to 99% by weight, preferably from 8 to 80% by weight;

(3) fatty acid residues constituting diglycerides contain 8 to 24 carbon atoms and a content of unsaturated fatty acid residues is 70% by weight or more based on the fatty acid residues; and (4) diglycerides comprise 40% by weight or less of saturated/unsaturated fatty acid diglycerides, 5% by weight or less of saturated/saturated fatty acid diglycerides and the balance of unsaturated/unsaturated fatty acid diglycerides.

When the diglyceride content in the fat and oil composition of the present invention is less than 5% by weight, dissolution of the phospholipid composition is poor in the resulting fat and oil composition. When the fat and oil composition contains a large amount of the diglyceride and the content of monoglycerides is also high, the fat and oil composition frequently shows fuming during heating. Thus it is particularly preferable that the diglyceride content ranges from 8 to 80% by weight. Similar to diglycerides, monoglycerides are effective in increasing the dissolution of phospholipids. However, differing from diglycerides, monoglycerides cause serious fuming during heating even contained in a small ratio (e.g., exceeding 10% by weight) in the fat and oil components. Therefore it is desirable to control the monoglyceride content in the fat and oil composition to 10% by weight or less, preferably 2% by weight or less.

On the other hand, edible fats such as butter, shortening and lard have been widely used as an edible fat composition. In these fields, it has also been urgently required to develop a fat composition having the above-mentioned cooking properties (i.e., oxidation stability and heat resistance) and digestion properties (i.e., showing no oily feel). This requirement may be satisfied by providing the fat composition according to the present invention having a diglyceride component satisfying the following characteristics:

(1) a weight ratio of diglycerides to monoglycerides ranges from 5:1 to 990:1;

(2) diglycerides are contained so as to give a content based on the total fat and oil content in the oil composition of from 5 to 99% by weight, preferably from 8 to 80% by weight;

(3) fatty acid residues constituting diglycerides contain 8 to 24 carbon atoms; and (4) diglycerides comprise 40% by weight or more of saturated/unsaturated fatty acid diglycerides, 5% by weight or more of saturated/saturated fatty acid diglycerides and the balance of unsaturated/unsaturated fatty acid diglycerides.

The content of the diglyceride component may preferably be elevated by adding fats rich in diglycerides which have been obtained by ester-exchanging a mixture of one or more fats or oil having a high unsaturated fatty acid residue content (for example, safflower oil, olive oil, cotton seed oil, rapeseed oil, corn oil, soybean oil, palm oil, rice bran oil, sunflower oil, sesame oil, lard, beef tallow, fish oil, butter or those obtained by fractionating, randomizing, hardening or ester-exchanging these fats or oils) with glycerol in a manner as disclosed, for example, in U.S. Pat. No. 4,976,984 or esterifying unsaturated fatty acids originating from these fats or oils with glycerol.

In order to describe the present invention in greater detail, and not by way of limitation, the following Examples will be given, wherein all % are by weight unless otherwise noted.

EXAMPLE 1

Highly pure soybean lecithin (SLP-WSP, trade name, manufactured by Tsuru Lecithin Kogyo K.K.; content of acetone-insoluble matters: 95% or more) was treated with phospholipase D in accordance with the manner as disclosed in JP-A-58-51835 and thus a phospholipid composition, wherein the content of the total nitrogen-containing phospholipids (for example, phosphatidylcholine (PC), phosphatidylethanolamine (PE), phosphatidylserine (PS), sphingomyelin (SM)) based on the total amount of phospholipids, glycolipids and sterol derivatives is controlled to 0.01 or less, was obtained. The phospholipid composition was further subjected to silica gel column chromatography using WAKOGEL C-200 (manufactured by Wako Pure Chemical Industries, Ltd.) as a carrier and chloroform/methanol (2/3) as an eluent and the fraction of the final high-polar substance was removed while confirming with TLC. Table 1 shows the composition of the phospholipid composition thus obtained.

Next, 0.2% of the phospholipid composition was blended with rapeseed oil containing 10% of rapeseed diglycerides so as to give an oil composition. The cooking properties of the obtained oil composition were evaluated. Table 2 shows the results.

EXAMPLE 2

The procedure of Example 1 was repeated except that the soybean lecithin was replaced by yolk lecithin (a purified yolk lecithin manufactured by Asahi Chemical Industry Co., Ltd.) to thereby give a phospholipid composition and an oil composition. Table 1 shows the composition of the phospholipid composition thus obtained, while Table 2 shows the results of the evaluation of the cooking properties of the obtained oil composition.

COMPARATIVE EXAMPLES 1 AND 2

The procedure of Example 1 was repeated except that the phospholipid composition was replaced by soybean lecithin (SLP-WSP, trade name, manufactured by Tsuru Lecithin Kogyo K.K.) (Comparative Example 1) or yolk lecithin (a purified yolk lecithin manufactured by Asahi Chemical Industry Co., Ltd.) (Comparative Example 2) to thereby give each an oil composition. Table 1 shows the composition of the soybean lecithin and that of the yolk lecithin, while Table 2 shows the results of the evaluation of the cooking properties of the obtained oil compositions.

COMPARATIVE EXAMPLE 3

Highly pure soybean lecithin (SLP-WSP, trade name, manufactured by Tsuru Lecithin Kogyo K.K.; content of acetone-insoluble matters: 95% or more) was treated with phospholipase D in accordance with the manner as disclosed in JP-A-58-51835 and thus a phospholipid composition, wherein the content of the total nitrogen-containing phospholipids (e.g., phosphatidylcholine (PC), phosphatidylethanolamine (PE), phosphatidylserine (PS), sphingomyelin (SM)) based on the total amount of phospholipids, glycolipids and sterol derivatives is controlled to 0.01 or less, was obtained. Table 1 shows the composition of the phospholipid composition thus obtained.

By using the obtained phospholipid composition, an oil composition was prepared by the same method as in Example 1. Table 2 shows the results of the evaluation of the cooking properties of this oil composition.

TABLE 1

| Sample | Example 1 | Example 2 | Comparative Example 1 | Comparative Example 2 | Comparative Example 3 |
|---|---|---|---|---|---|
| Nitrogen-containing phospholipid: | | | | | |
| PC content (% by weight) | Trace | Trace | 24 | 70 | Trace |
| PE content (% by weight) | Trace | Trace | 18 | 15 | Trace |
| PS content (% by weight) | Trace | Trace | 2 | — | Trace |
| SM content (% by weight) | Trace | Trace | Trace | 3 | Trace |
| PA + LPA content (% by weight) | 90 | 90 | 6 | — | 90 |
| Glycolipid content (% by weight) | 3 | 1 | 12 | — | 3 |
| Sterol derivative content (% by weight) | 1 | 2 | 3 | 2 | 1 |
| High-polar substance content*[1] (area/μg) | 20 | 100 | 2000 | 600 | 1000 |

Note; *[1]The high-polar substances given in Table 1 were determined by the following method. HPTLC Silica Gel 60 (trade name, a product manufactured by Merck & Co., Inc.) was used as a silica gel plate. Each sample was dissolved in chloroform/methanol (2:1) in such a manner as to give a concentration of about 20 mg/ml. 2 μl of the sample solution was accurately charged on the plate. Then it was developed with a solvent (chloroform/acetone/methanol/acetic acid/water = 10/4/2/2/1). Next, the plate was uniformly color-developed by immersing a color development solution (methanol/water/sulfuric acid = 90/90/6) for 5 seconds and then heating on a hot plate or in an oven at 120° C. for 10 minutes. The color-developed plate thus obtained was subjected to measurement with a TLC scanner within one hour. The employed TLC scanner was a TLC Scanner CS-9000 provided with a xenon lamp (a product manufactured by Shimadzu Corporation). The determination conditions as follows.
Photo mode: Abs refraction
Scan mode: Zig-Zag scan
Determination wavelength: 540 nm
Zero set mode: B.C.
Swing Width: 8.0 mm The area of substances hardly shifting from the original point (Rf value of the peak: 0–0.1) per μg of the sample charged on the plate was referred to as the amount of high-polar substances (area/μg),

TABLE 2

| Example No. | Evaluation of cooking properties (in frying)*[1] | | |
|---|---|---|---|
| | Smell during heating*[2] | Coloration of Oil after heating*[3] | Flavor*[4] |
| Example 1 | A | A | A |
| Example 2 | A | A | A |
| Comparative Example 1 | B | B | B |
| Comparative Example 2 | B | B | B |

TABLE 2-continued

| Example No. | Evaluation of cooking properties (in frying)*[1] | | |
|---|---|---|---|
| | Smell during heating*[2] | Coloration of Oil after heating*[3] | Flavor*[4] |
| Comparative Example 3 | B | B | B |

Note;
*[1]The cooking properties (in frying) were evaluated in the following manner:
Oil temperature: 180° C. (gas caloric force: 0.50 l/min)
Oil amount: 500 g
Total cooking time: 20 minutes
Cooking method:
500 g of each oil composition obtained in the above Examples or Comparative Examples was introduced into a frying pan and the oil temperature was adjusted to 180° C. Next, the following materials were coated with the composition as specified below and then fried in the oil.
Materials:
Green pepper: 4 pieces of ½-cut
Egg plant: 3 pieces of ¼-cut
Sweet potato: 3 slices (each 5 mm in thickness)
Prawn (medium-size): 3
Coating composition: (mixed while cooling in an ice/water bath)
Soft flour: 100 g
Water: 140 g
Whole egg: 25 g
*[2]Evaluation criteria for smell during heating:
A: good
B: poor
*[3]Evaluation criteria for coloration of oil:
A: not colored
B: colored
*[4]Evaluation criteria for flavor:
A: good
B: oily

REFERENTIAL EXAMPLE 1

10 g of the phospholipids containing PA and L-PA obtained in Comparative Example 3, which had been treated with an enzyme such as phospholipase D, were dissolved in 100 ml of n-hexane so as to give a concentration of 10% (wt/vol). To the hexane solution thus obtained, 20 ml of ethanol was added. Further, 30 ml of a 1.5M aqueous solution of calcium chloride was added thereto. Then 1N NaOH was added dropwise to the mixture under stirring until the pH value reached 10. After 4 hours, the stirring was ceased and the mixture was centrifuged in a 50 ml centrifugation tube at 3,000 rpm for 10 minutes at 25° C. The upper hexane layer was collected thereby 90 ml of a phospholipid calcium salt fraction was obtained. After adding 45 ml of ethanol, the mixture was stirred and then centrifuged at 3,000 rpm for 10 minutes at 25° C. Thus calcium salts of PA and L-PA were obtained as a precipitate. The precipitate thus obtained was dissolved by adding 81 ml of n-hexane and then 40.5 ml of ethanol was added thereto. After stirring and centrifuging at 3,000 rpm for 10 minutes at 25° C., purified calcium salts of PA and L-PA were obtained as a precipitate.

The precipitate thus obtained was dissolved in 100 ml of n-hexane again and insoluble matters were removed. Further, the hexane was removed with an evaporator. Thus 6 g of calcium salts of PA and L-PA were obtained.

REFERENTIAL EXAMPLE 2

10 g of the phospholipids containing PA and L-PA obtained in Comparative Example 3 were dissolved in 100 ml of n-hexane so as to give a concentration of 10%

(wt/vol). To the hexane solution thus obtained, 20 ml of ethanol was added. Further, 30 ml of a 1.5M aqueous solution of calcium chloride was added thereto. Then 1N NaOH was added dropwise to the mixture under stirring until the pH value reached 10. After 4 hours, the stirring was ceased and the mixture was centrifuged at 3,000 rpm for 10 minutes at 25° C. The upper hexane layer was collected thereby 90 ml of a phospholipid calcium salt fraction was obtained. Then 36 g of triglycerides derived from rapeseed oil were added thereto and the mixture was stirred and then centrifuged at 3,000 rpm for 10 minutes at 25° C. Thus calcium salts of PA and L-PA were obtained as a precipitate. The precipitate thus obtained was dissolved by adding 81 ml of n-hexane and then 32.4 g of triglycerides derived from rapeseed oil were added thereto. After stirring and centrifuging at 3,000 rpm for 10 minutes at 25° C., purified calcium salts of PA and L-PA were obtained as a precipitate. The precipitate thus obtained was dissolved in 100 ml of n-hexane again and insoluble matters were removed. Further, the hexane was removed with an evaporator. Thus 6 g of calcium salts of PA and L-PA were obtained.

REFERENTIAL EXAMPLE 3

The purification of PA with the use of a silica gel column is given as a referential example.

73.5 g of the natural phospholipids containing PA obtained in Comparative Example 3, which had been treated with an enzyme such as phospholipase, were dissolved in 50 ml of n-hexane and then added dropwise to 250 ml of acetone which had been ice-cooled in an acetone/dry ice bath. After centrifuging in a 500 ml tube at 3,000 rpm for 10 minutes, 200 ml of ice-cooled acetone was added to the resulting pasty precipitate. Then the mixture was centrifuged again at 3,000 rpm for 10 minutes and the precipitate was desolvated with an evaporator. Thus 55.41 g of acetone-insoluble matters were obtained.

The acetone-insoluble matters were dissolved in 70 ml of chloroform and divided into portions each weighing 52 g, followed by fractionating with the use of three columns. The amount of the solvent used for each column (WAKOGEL C-200; 800 g) is given below. PA was eluted by using a chloroform/methanol mixture as a solvent with varying the mixing ratio thereof. The mixing ratio and amounts of the solvents are as follows.

| 1. Sample charge | 52 g |
| 2. Chloroform/methanol = 5/1 | 200 ml |
| 3. Chloroform/methanol = 2/1 | 4500 ml |
| 4. Chloroform/methanol = 3/2 | 4200 ml |
| 5. Chloroform/methanol = 1/1 | 1800 ml |
| 6. Chloroform/methanol = 2/3 | 600 ml |

The solvents passed through the columns were divided into portions of each 450 ml and each portion was analyzed. As a result, it was found that PA was eluted in the second half of the fraction of the chloroform/methanol ratio of 2/1 to the first half of the fraction of said ratio of 1/1. 3,600 ml of a fraction eluted with the chloroform/methanol mixture of 3/2 showing a particularly high purity of PA was collected and desolvated with an evaporator to thereby give purified PA. Thus 19.67 g of purified PA was obtained in total by this method. The total amount required for the purification was 34,770 ml (20,698 ml of chloroform, 13,572 ml of methanol, 450 ml of acetone and 50 ml of n-hexane).

The amounts of the solvents required for purifying 1 g of PA and/or L-PA in Referential Example 1 and Referential Example 3 were compared. Table 3 shows the results.

TABLE 3

| | Referential Example 1 | Referential Example 3 |
|---|---|---|
| Amount of solvent required for purifying 1 g of PA and/or L-PA (ml/g) | 59.7 | 1767.1 |
| Purity of PA and/or L-PA (%; determined by HPLC) | 99 | 99 |

As the above results show, the process of the present invention makes it possible to obtain PAs and/or L-PAs of high purity on an industrial scale.

EXAMPLE 3

Soybeans produced in China (Konan No. 2) were employed as the oilseed. These soybeans were ground in a Waring blender. 20 g of the ground matters thus obtained were packed in a glass column (50 ml) and then 120 ml of a 0.1M sodium acetate/acetic acid buffer solution (pH 6.0) was passed through the column. The eluate was permeated through a membrane of a fractionation molecular weight of 13,000. Thus a clear extract was obtained.

20 g of commercially available defatted lecithin (manufactured by Tsuru Lecithin Kogyo K.K.) was fed into a 300 ml four-neck flask provided with a stirrer. 120 ml of the above-obtained extract (pH 6.0) was added thereto. Then the mixture was continuously stirred for 24 hours while maintaining the reaction system at 30° C. under a nitrogen gas stream (100 ml/min.). After the completion of the reaction, the mixture was heated to 70° C. for 1 hour and cooled. Then 65 ml of ethanol was added thereto and the mixture was extracted with 150 ml of hexane.

150 ml of the hexane extract obtained above was fed into a 300 ml four-neck flask provided with a stirrer. Then 25 ml of ethanol, 15 ml of water and ½ times by volume of calcium chloride, based on the solid matters in the hexane extract, were added thereto. The pH value of the mixture was adjusted to 10.0 by adding a 1N solution of sodium hydroxide under stirring at room temperature. After aging by stirring for additional 4 hours, the mixture was centrifuged to thereby give a hexane solution.

To 150 ml of the aforesaid hexane solution, 75 ml of ethanol was added to thereby effect solvent-precipitation. Then the supernatant was removed by centrifuging. The precipitate was dissolved by adding hexane and thus the total volume was adjusted to 75 ml. The hexane solution was washed with a 50% ethanol/water under an acidic (hydrochloric acid) condition of pH value of 1 at 15° C. by stirring for 10 minutes. After separating, the obtained hexane phase was neutralized with an aqueous solution of sodium hydroxide and desolvated to thereby give PA.

The precipitate formed in the aforesaid solvent-precipitation was weighed. Further, the heat coloration property of the obtained PA were evaluated by the method as specified below. Table 4 summarizes the results.

Evaluation of heat coloration property 0.025 g of PA was introduced into a test tube. 10 g of rapeseed oil containing 10% of diglyceride was added thereto and the PA was dissolved by stirring. The obtained solution was heated to 180° C. for 70 minutes on a block heater and then the color difference in comparison with hexane was measured with a color difference meter (SZ-Σ80, manufactured by Nippon Denshoku Kogyo K.K.). The ΔE(H) value thus determined was referred to as the hue value.

REFERENTIAL EXAMPLE 4

150 ml of the hexane extract obtained in Example 3 was introduced into a 300 ml four-neck flask provided with a stirrer and 25 ml of ethanol and 15 ml of water were added thereto. Then the pH value of the mixture was adjusted to 10.0 by adding a 1N solution of sodium hydroxide under stirring at room temperature. After aging by stirring for additional 4 hours, the mixture was centrifuged to thereby give a hexane solution. To 150 ml of this hexane solution, 75 ml of ethanol was added. The precipitate formed at the addition of ethanol was weighed. Table 4 shows the results.

REFERENTIAL EXAMPLE 5

150 ml of the hexane extract obtained in Example 3 was introduced into a 300 ml four-neck flask provided with a stirrer and 25 ml of ethanol, 15 ml of water and ½ times by volume of calcium chloride, based on the solid matters in the hexane extract, were added thereto. After aging by stirring for additional 4 hours, the mixture was centrifuged to thereby give a hexane solution. To 150 ml of this hexane solution, 75 ml of ethanol was added. The precipitate formed at the addition of ethanol was weighed. Table 4 shows the results.

REFERENTIAL EXAMPLE 6

75 ml of the hexane extract obtained in Example 3 was washed with a 50% ethanol/water by stirring under an acidic (hydrochloric acid) condition of pH value of 1 at 15° C. for 10 minutes. After separation, the obtained hexane phase was neutralized with an aqueous solution of sodium hydroxide and desolvated to thereby give PA. The heat coloration properties of this PA were evaluated by the same method as in Example 3. Table 4 shows the results.

TABLE 4

|  | Precipitate (g) | Heat Coloration Property (hue after heating) |
| --- | --- | --- |
| Example 3 | 7.5 | 10 |
| Referential Example 4 | 0 | — |
| Referential Example 5 | 0 | — |
| Referential Example 6 | 0 | 30 |

It is apparent that the present invention enables the blending of phospholipids with a frying oil, which has been considered difficult since it causes heat coloration. Thus, an oil composition, which is excellent in mold-release characteristics during cooking, has a good smell during heating, suffers from no coloration of oil after heating and shows a good flavor, can be obtained.

Further, the process of the present invention gives PAs and L-PAs of high purity and contaminated with no impurities in a high yield through simple handling as compared to the conventional purification method using column chromatography, thus the process of the present invention is highly useful for industrial production of PAs and L-PAs.

While the invention has been described in detail and with reference to specific examples thereof, it will be apparent to one skilled in the art that various changes and modifications can be made therein without departing from the spirit and scope thereof.

What is claimed is:

1. A process for producing phosphatidic acids and/or lysophosphatidic acids comprising
   (a) purifying a phospholipid mixture containing a phosphatidic acid and/or a lysophosphatidic acid by
      (1) dispersing or dissolving the phospholipid mixture containing the phosphatidic acid and/or the lysophosphatidic acid in water or a nonpolar solvent and then
      (2) reacting the phosphatidic acid and/or the lysophosphatidic acid with an aqueous solution of a polyvalent metal salt in the presence of a polar solvent under an alkaline condition to thereby give rise to a polyvalent metal salt of the phosphatidic acid and/or the lysophosphatidic acid;
      (3) adding a substance capable of precipitating a polyvalent metal salt of a phosphatidic acid and/or a lysophosphatidic acid to said polyvalent metal salt of the phosphatidic acid and/or the lysophosphatidic acid obtained in said step (a)(2) in the presence of a nonpolar solvent to precipitate said polyvalent metal salt of the phosphatidic acid and/or the lysophosphatidic acid and then
      (4) separating the resulting precipitated polyvalent metal salt of the phosphatidic acid and/or the lysophosphatidic acid,
   (b) washing the resulting polyvalent metal salt of the phosphatidic acid and/or the lysophosphatidic acid obtained in said step (a)(4) with an aqueous water-soluble solvent under an acidic condition,
   wherein said substance capable of precipitating a polyvalent metal salt of a phosphatidic acid and/or a lysophosphatidic acid is a lipid or a polar solvent containing 1 to 10 carbon atoms and having a polar group, and wherein said lipid is a monoglyceride, a diglyceride, a triglyceride or a mixture thereof.

2. A process of claim 1, wherein said polyvalent metal forming said polyvalent metal salt is an element belonging to the group IIA or group IIIB.

3. A process of claim 1, wherein said nonpolar solvent is a liquid organic compound containing 5 to 16 carbon atoms and having a dielectric constant of 10 or below.

4. A process of claim 3, wherein said liquid organic compound having a dielectric constant of 10 or below is a hydrocarbon or a substituted hydrocarbon.

5. A process of claim 1, wherein said polar solvent is a liquid organic compound containing 1 to 10 carbon atoms and having a dielectric constant exceeding 10.

6. A process of claim 5, wherein said liquid organic compound having a dielectric constant exceeding 10 is a monohydric alcohol, a polyhydric alcohol or a ketone.

7. A process of claim 1, wherein said polar solvent containing 1 to 10 carbon atoms and having a polar group is a liquid organic compound having a dielectric constant exceeding 10.

8. A process of claim 7, wherein said liquid organic compound having a dielectric constant exceeding 10 is a monohydric alcohol, a ketone, a polyhydric alcohol or a mixture thereof.

9. A process of claim 1, wherein a pH value of said alkaline condition is from 7 to 12 and said polyvalent metal salt of the phosphatidic acid and/or the lysophosphatidic acid obtained in said step (a) is aged for 0.5 hour or longer under stirring in the presence of said nonpolar solvent before adding said substance capable of precipitating a polyvalent metal salt of a phosphatidic acid or a lysophosphatidic acid.

10. A process of claim 1, wherein the washing with an aqueous water-soluble solvent is performed at a pH value of 0.5 to 5 and at a temperature of 0° to 40° C. with the use of 5 or more times by weight, based on solid matters, of said aqueous water-soluble solvent.

11. A process of claim 10, wherein said aqueous water-soluble solvent is a liquid organic compound containing 1 to 10 carbon atoms and having a dielectric constant exceeding 20.

12. A process of claim 11, wherein said liquid organic compound having a dielectric constant exceeding 20 is a monohydric alcohol, a polyhydric alcohol or a ketone.

13. A process of claim 10, wherein a water-soluble solvent contained in said aqueous water-soluble solvent is ethanol.

14. A process of claim 11 or 12, wherein a water-soluble solvent contained in said aqueous water-soluble solvent is ethanol.

15. A process of claim 10, wherein a weight ratio of water to a water-soluble solvent in said aqueous water-soluble solvent is 5 to 80% by weight.

16. A process of claim 1, wherein said phospholipid mixture containing the phosphatidic acid and/or the lysophosphatidic acid is obtained by treating lecithin with ground oilseeds or an oilseed extract.

17. A process of claim 16, wherein said ground oilseeds are obtained by grinding an oilseed and said oilseed extract is obtained by extracting ground oilseeds.

18. A process of claim 17, wherein said oilseed extract is further subjected a penetration purification through a membrane.

* * * * *